United States Patent [19]
Webster

[11] Patent Number: 5,616,865
[45] Date of Patent: Apr. 1, 1997

[54] ACOUSTIC WAVE GENERATING APPARATUS

[75] Inventor: John M. Webster, New York, N.Y.

[73] Assignee: Holographics Inc., Long Island City, N.Y.

[21] Appl. No.: 408,650

[22] Filed: Mar. 22, 1995

Related U.S. Application Data

[62] Division of Ser. No. 157,815, Nov. 24, 1993, Pat. No. 5,505,090.

[51] Int. Cl.$^6$ .............................. H01J 17/00; H01S 4/00
[52] U.S. Cl. ................. 73/627; 313/325; 372/87
[58] Field of Search .......................... 73/627, 625, 626, 73/642, 606, 608, 657; 313/359.1, 230, 325; 372/76, 86, 87, 73

[56] References Cited

U.S. PATENT DOCUMENTS

| | | | |
|---|---|---|---|
| 3,428,940 | 2/1969 | Huckabay | 367/147 |
| 4,161,121 | 7/1979 | Zitelli et al. | 73/626 |
| 4,276,491 | 6/1981 | Daniel | 73/626 |
| 4,470,308 | 9/1984 | Hayakawa et al. | 73/626 |
| 4,651,311 | 3/1987 | Owen et al. | 367/147 |
| 5,280,724 | 1/1994 | Higo et al. | 73/625 |

*Primary Examiner*—Hezron E. Williams
*Assistant Examiner*—Helen C. Kwok
*Attorney, Agent, or Firm*—Brumbaugh, Graves, Donohue & Raymond

[57] ABSTRACT

Apparatus for non-destructively inspecting for faults in or beneath the surface of structures, such as debonds or delaminations in composite materials, or cracks, broken stringers, delaminations and the like in semi-monocoque structures, includes at least one spark gap discharge device displaced from the test object which focuses an acoustic pulse onto a small local area of the object for vibrationally exciting the surface of that area. A laser Doppler camera system, also displaced from the test object directs a laser beam onto the excited area and derives from light energy reflected back from the excited area the velocity of out-of-surface displacement of, and relaxation frequencies generated by, the surface of the excited area and provides an indication of whether a fault is present in that area. Acoustic pulses and the laser beam are directed to successive local areas in synchronism according to a scanning pattern, at each of which the reflected light energy is analyzed, following which the acquired data is processed and visually displayed in a manner which clearly indicates the presence of a fault and its location and enables the operator to further analyze the data to ascertain the type and extent of the fault.

10 Claims, 4 Drawing Sheets
(1 of 4 Drawing(s) in Color)

ACOUSTIC WAVE GENERATING APPARATUS

This application is a division of application Ser. No. 08/157,815, filed on Nov. 24, 1993, U.S. Pat. No. 5,505,090.

BACKGROUND OF THE INVENTION

This invention relates generally to non-destructive inspection of structures and, more particularly, to methods and apparatus for non-destructively inspecting for debonding and delamination faults in composite materials and for structural faults in monocoque and semi-monocoque structures.

Advances in modern composites have made it possible to introduce high strength/weight ratio materials into highly stressed critical components such as those used in aircraft and weapons, for example. The development of alternative resin systems has also greatly improved the flexibility of manufacturing such structures. Tough, high strength, high temperature thermoplastic polymers combined with advanced graphite fibers have made it possible to consider structures of a size and strength heretofore considered economically impractical. In the aircraft industry, for example, where composite materials are increasingly being used, the size of composite structures range from relatively small control surfaces on drones, targets and missiles to the very large surfaces of vertical stabilizer, aileron and wing control elements on military and commercial aircraft; future applications include fuselage structures.

Such composite materials have failure modes quite different from metals and alloys in that they suffer from delamination, debonding and cracking, as well as deterioration from fatigue and ambient exposure. In addition to failure in service, these materials may also suffer from defects in manufacturing similar to those which occur under field stresses. Thus, a practical technique is needed for non-destructively locating faults in composite structures which is suitable not only for in-plant non-destructive evaluation but for field use as well.

Among known techniques for detecting delamination or debonding is that known as acoustic "scrubbing" wherein a small instrument containing an acoustic crystal is manually scanned across the surface of the object under examination while "listening" for anomalies in the sound. For small objects, this process is simple and efficient, but is much too time-consuming, and therefore prohibitively expensive, to be practical for evaluation of large components and structures.

Another suggested technique is to heat part or all of the surface of the component by flash discharge lamps and after a predetermined delay making an infrared photograph of the surface with a CCD camera system. This system is premised on the assumption that decay of the surface temperature during the delay period is a function of the thickness and thermal conductivity of the material, factors which would be affected by debonds or delaminations and cause anomalies in the photograph. The effectiveness of this system is highly dependent on the surface finish or condition of the object.

Perhaps the simplest, yet most effective, technique that has been proposed is to simply tap the surface of the structure at different spots and listen to the resulting sound; a dead or hollow sound indicates a fault condition, as opposed to a sharp sound in a fault-free area. This technique, too, is very time-consuming and the evaluation is very subjective, making it impractical for evaluation of most structures.

Faults occurring in monocoque and/or semi-monocoque structures, basically a skeleton over which a skin is secured and of which an aircraft fuselage is a practical example, are manifested in much different ways than in composite structures. If the skin develops cracks, or is weakened or becomes detached from the skeletal framework, then a rupture can result causing impairment of the entire structure, particularly if it is an aircraft fuselage which is usually pressurized. Similarly, if the underlying skeletal structure cracks, or becomes corroded, or the fastening system fails, structural failure can result.

The difficult task of inspecting the substructure of the skin of an aircraft fuselage for corrosion, broken fastenings, cracks or loose rivets is effectively performed by the method described in applicant's copending U.S. patent application Ser. No. 08/011,991 filed Feb. 1, 1993. The therein disclosed non-destructive inspection method includes the steps of mechanically exciting, with an exciter affixed to the object, a vibrating nodal pattern in the outer skin of a monocoque structure, panels of which may freely vibrate at one or more resonant frequencies. The frequency of excitation is scanned through a spectrum which includes such resonant frequencies and is locked onto a resonant frequency which is uniquely characteristic of a certain phase relationship of the anti-nodes of the nodal pattern. The amplitude of the excitation is then varied until the anti-nodes of the pattern are optimized to be either bi-concave or concave/convex, and when such optimization occurs two time-displaced holograms of the vibrating outer skin are recorded in synchronism with maximum plus and minus displacement, respectively, of an anti-node. It is from this fringe map of contour patterns, which is uniquely characteristic to any given structural condition, that faults are interpreted.

The speed and accuracy of analysis of the results produced by this vibrational technique for detection of flaws is improved by the system described in U.S. patent application Ser. No. 08/108,123 filed by applicant and another on Aug. 17, 1993, the disclosure of which is incorporated herein by reference. It is a computer-based system which analyzes nodal patterns induced in the surface of a structure being inspected either by analyzing a record obtained by interferometry, or by directly scanning, or digitally interrogating point-by-point, the vibrating surface of the structure with a beam of quasi-coherent radiant energy and, utilizing the Doppler effect, reading the out-of-phase displacement of the surface to produce a visual contour map of the surface for capture and computer analysis. Alternatively, a computer may be programmed to either directly capture the nodal pattern and provide either a direct readout of the location and/or identity of faults, or directly capturing the nodal pattern for later processing.

Unfortunately, the just-described techniques for locating faults in semi-monocoque structures do not always effectively reveal debonding and delamination faults in composite materials, and, conversely, known techniques for non-destructively inspecting composite materials are inapplicable to semi-monocoque structures, in addition to being less than ideal for their intended usage. There is therefore a need for a non-destructive evaluation technique, suitable for both in-plant and field use, for non-destructively inspecting for faults in composite materials, semi-monocoque structures and monocoque structures, large or small.

SUMMARY OF THE INVENTION

Briefly, this need is satisfied by a computer-based system which exploits the changes in vibration characteristics or nodal response of the surface of a vibrationally-excited structure caused by internal defects. The vibration is preferably induced by acoustic pulses generated by a remote source which scans an area of the surface of the structure point-by-point, both vertically and horizontally. The amplitude of the out-of-plane displacement of the surface, and/or acoustic emissions from the surface, are remotely measured point-by-point with a computer-controlled laser Doppler vibrometer system which scans the surface in synchronism with the scanning of the acoustic pulses. The Doppler process detects the small shifts in laser wavelength caused by the movement of the object from which out-of-plane displacement is derived. A laser profiling system interfaced with the laser Doppler system supplies data to the computer necessary to compute displacement, or where the object displacement plane is not perpendicular to the vibrometer axis, amplitude, etc. of a surface of convoluted shape for insuring that point-to-point variations detected by the Doppler process are due only to variations in surface displacement, and not because of differences in the angle of incidence of the object plane.

The surface displacement information gathered by the scanning laser Doppler vibrometer system, which may be read either digitally or in analog form, is utilized to generate a plot of the surface of the object under inspection, which gives a picture of the object with fault identification, or, alternatively, the Doppler output may be superimposed on a secondary optical image of the surface produced by other means, such as a charged coupled device (CCD) camera. In either case, fault location and its extent can be coded onto the image either in quantitative form or by color contouring in an analog display. By comparison of signal amplitude, direction of surface movement and the relaxation frequencies produced by a fault with signals produced by non-fault areas, the extent of that fault may be compared to a library store of information for material of that particular type, and the diagnosis displayed with a visual display unit (VDU) or separate readout.

The Doppler vibrometer analysis technique has the advantageous capability of remotely studying both surface displacement and the relaxation frequencies of the object under analysis after being excited by a suitable excitation pulse. Using high energy acoustic pulses to excite the object, a fault point can be located and its relaxation frequencies may be recorded during a scan or, if desired, subsequent to the scan, after the location of the fault has been ascertained. Importantly, the analysis of relaxation frequencies in a fault made during or subsequent to a typical Doppler scan is also applicable to the inspection of semi-monocoque or monocoque structures manufactured with composites and other materials.

A condition closely simulating "tapping" of the surface of the object is achieved with an acoustic shock-wave focused on a relatively local area generated by a focused or phased array of discharge devices each comprising an insulator within which an external capacitor is rapidly discharged through a small diameter tube. The discharge is of short duration, usually less than 10 μsec, and the emergent high-energy shock or acoustic wave is quasi-unidirectional. In other words, the energy is emitted substantially in a forward direction, i.e., substantially unidirectionally.

BRIEF DESCRIPTION OF THE DRAWINGS

The file of this patent contains one drawing executed in color. Copies of this patent with the color drawing will be provided by the Patent and Trademark Office upon request and payment of the necessary fee.

Other objects, features and advantages of the invention will become apparent, and its construction and operation better understood, from the following detailed description when read with reference to the accompanying drawings, in which.

DESCRIPTION OF THE PREFERRED EMBODIMENT

Figure 1:
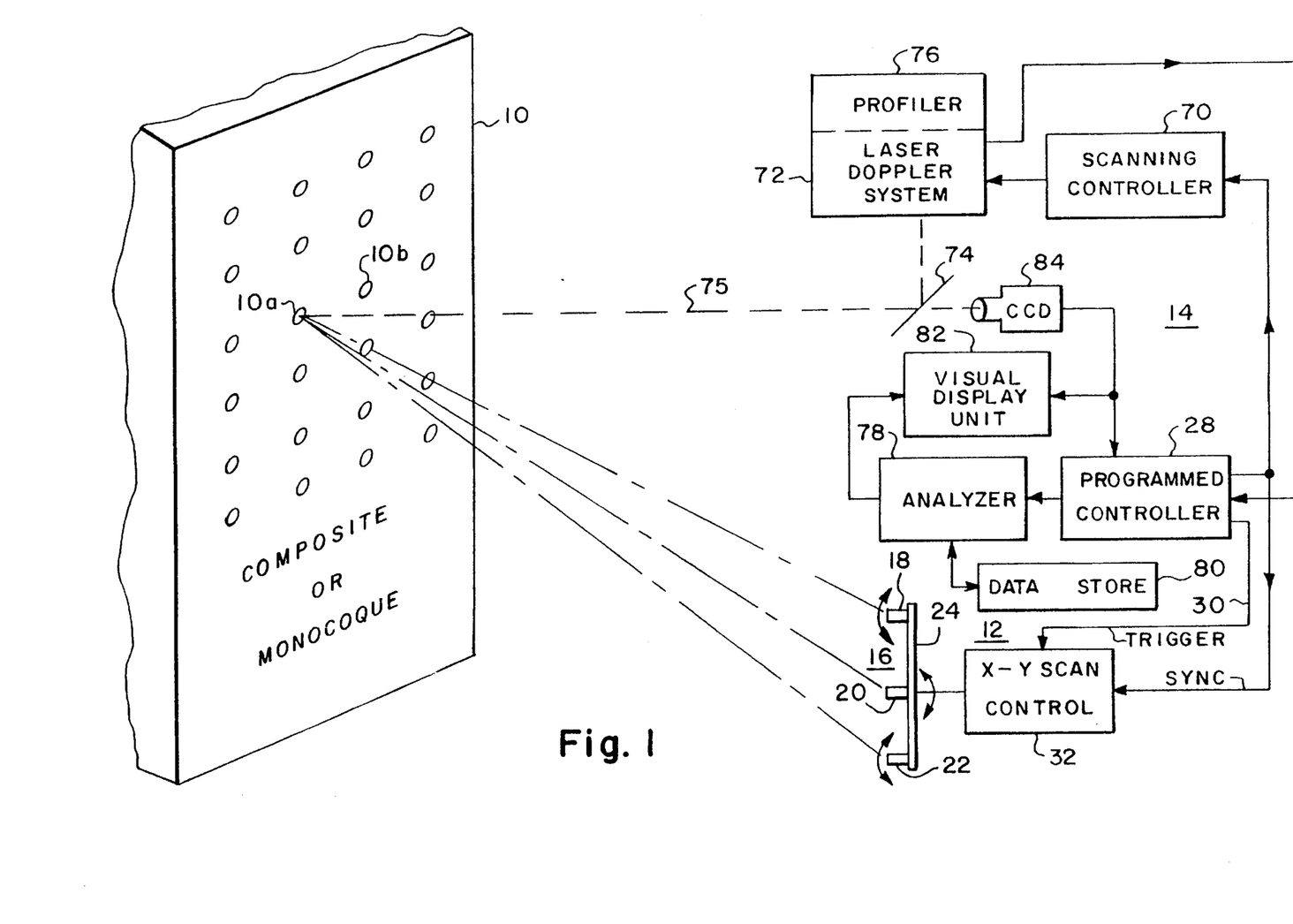
FIG. 1 is a diagrammatic block diagram (partially schematic) of a system embodying the principles of the invention for non-destructively inspecting a structure.

FIG. 1 is a diagrammatic block diagram of a system for performing substantially quasi-real-time analysis of structural faults in an object or structure 10, which may be a section of composite material or a monocoque or a semi-monocoque structure. The system consists of two basic subsystems: a system 12 located remotely from the structure for vibrationally exciting the surface point-by-point with acoustic pulses; and a laser Doppler system 14 which scans the surface of object 10, in synchronism with the point-by-point scanning of the acoustic pulses, for measuring out-of-plane surface displacement of successive points and providing a visual display of the location and extent of any structural faults.

For simplicity of illustration, a supporting structure 24 is shown somewhat remote from the laser doppler system 14. However, it should be understood that the systems 12 and 14 are preferably closely spaced with the supporting structure 24 generally parallel to the plane of the test object 10. Note also that the acoustic pulses generated by discharge devices 18, 20 and 22 travel substantially undirectionally from the devices as described in more detail below.

Figure 3:
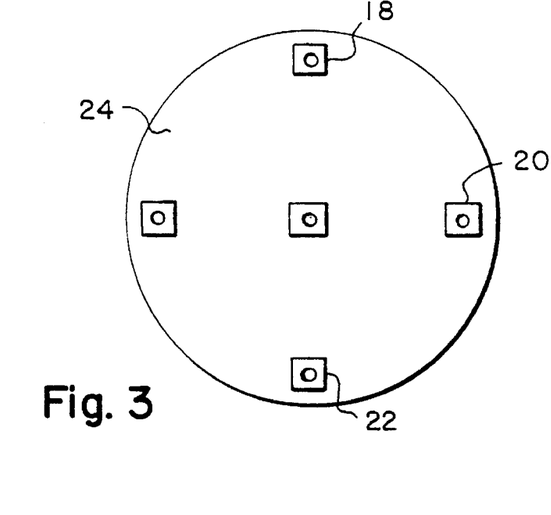
FIG. 3 is a diagrammatic front view of the array of acoustic pulse generating devices shown in elevation in FIG. 1.
Figure 4:
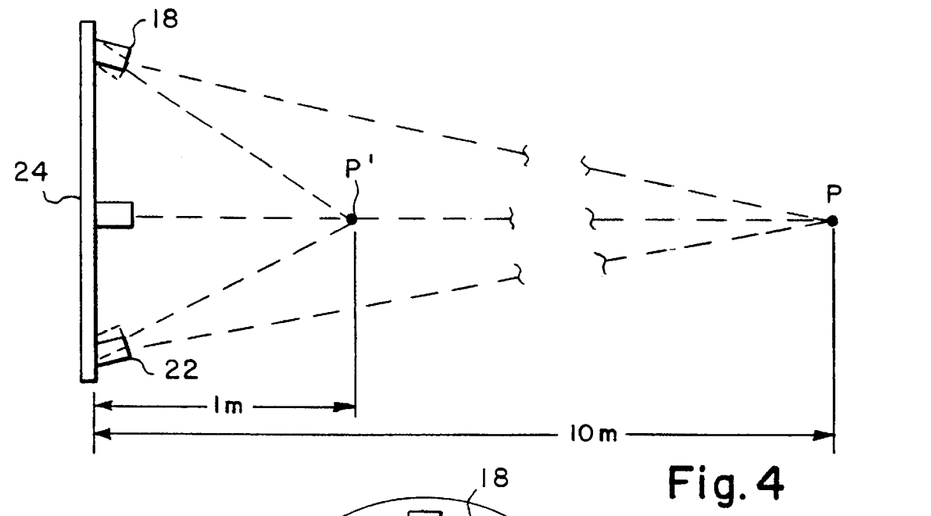
FIG. 4 is an elevation side view illustrating the variable focusing of the array of acoustic pulse generating devices shown in elevation in FIG. 1.

Considering first the remote acoustic pulse generating and scanning system 12, a high energy acoustic shock-wave is focused onto a relatively small localized area 10a on the surface of object 10 by an array 16 of discharge devices, mounted on a suitable supporting structure 24. The array 16 may comprise any number of discharge devices, for example, five arranged as shown in FIG. 3, i.e., with four of them equally spaced along a circle and a fifth supported at the center of the circle. Three of the five discharge devices are visible in FIG. 1 at 18, 20 and 22. As indicated by the arrows adjacent devices 18 and 22 in FIG. 1, the supporting structure 24 includes means such as motors (not shown) for controlling the structure 24 and for controlling the distance and directivity axis of the discharge devices so as to variably focus them (as shown by arrows) at a point along the Z-axis so that acoustic pulses produced simultaneously by each discharge device of the array converge at the same point on the surface of the test object at the same time. This adjustability of the focal point of the array allows the system to inspect an object over a range of distances from the object, say, from one meter to ten meters as depicted in FIG. 4 or further, in fact, to a collimated condition of infinity focus. As will be described in detail presently, each of the discharge devices generates high energy acoustic pulses of short duration, for example, less than 1 μsec. at source, to several milliseconds, at a predetermined repetition frequency, typically 100 pulses per second although far higher frequencies in the kilohertz range can be used, under control of trigger pulses supplied to them all from a programmed controller 28 via line 30 and applied to the arrayed discharge devices through an X-Y scan control system 32. The scan control system scans the focal point of the array 16 over a selected area of the test object according to a predetermined pattern, typically horizontally and vertically as indicated, in stepwise fashion, for example, from small area 10a to small area 10b, etc. The discharge devices are triggered at the correct moment so that an acoustic pulse is launched to cause the acoustic wave to impinge on a desired area 10a, for example. The X-Y scan control system 32 is preferably electrically controlled from a range finder system (not shown) to insure that a sharp focus at each point on the object is obtained as the distance from the array changes as the array is tilted during scanning. Each focused acoustic shock-wave excites a relatively small local area 10a, 10b, etc. of the surface of the object in a manner closely simulating that produced by "tapping" with an implement such as a rod or pencil, producing, following the pulse, relaxation frequencies having characteristics uniquely indicative of the presence of a rupture or fault.

Figure 2:
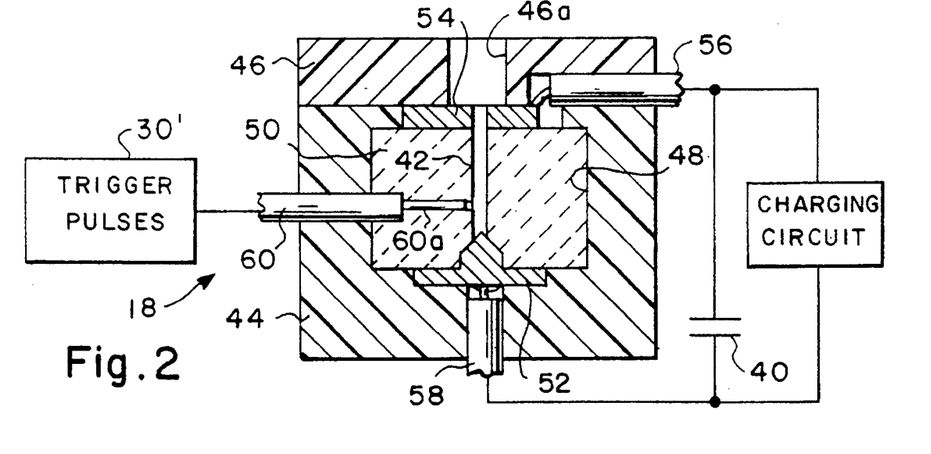
FIG. 2 is an elevation cross-section of a discharge device for generating high energy acoustic pulses.

In accordance with an important aspect of the invention, each of the discharge devices of the array 16, one of which is shown in cross-section in FIG. 2, produces a high energy quasi-unidirectional airborne acoustic pulse or wave by discharging an electrical capacitor 40 through a small diameter bore 42, one end of which is open to the atmosphere and the other end of which is closed. More particularly, the currently preferred discharge device comprises a cylindrical enclosure 44 having a-circular cover 46, both formed of a durable electrically insulating material and defining a central internal cylindrical cavity 48 within which a cylindrical insulator 50 is supported. For example, the insulator 50 may be 1⅛ inches long and 1¾ inches in diameter, and is also formed of electrically insulating material such as a hard ceramic, hard crystal such as quartz or sapphire, or hard heat-resistant plastic, or any such material, which will withstand repeated high energy spark discharges. The open end of the bore 42 typically may have a diameter on the order of one to two millimeters. An insulating cap 46 with a large opening 46a may be fitted on the unit. A cathode electrode 52, in the form of a metal disk having a central protrusion extending into a conforming hole formed in insert 50, seals the other end of the bore 42. An anode 54 in the form of an annular metal ring having an inside diameter substantially equal to that of bore 42, surrounds the open end of the bore and is held in firm contact with insert 50 by cover 46. A first conductor 56 extends radially through an opening formed in cover 46 and connects anode 54 to one terminal of capacitor 40, and the other terminal is connected to cathode 52 by a second conductor 58 which extends axially through a central opening formed in the closed end of enclosure 44. A third insulated conductor 60 has a bare portion 60a which extends through a radially extending bore formed in insulator 50 which terminates near the wall of bore 42 at a point some distance from cathode 52 to the anode 54. Conductor 60 is connected to a source 30' of short duration voltage trigger pulses which, as has been previously indicated, may have a high repetition frequency in excess of one kilohertz, for example. Other repetition frequencies as low as from 1 to 100 pulses per second can be used. The source 30' may be the line 30 by which programmed controller 28 supplies trigger pulses to X-Y scan control 32.

Although illustrated as a single capacitor, in a practical implementation capacitor 40 may be a bank of parallel-connected capacitors having circuit inductance values so as to be charged and discharged sufficiently rapidly to achieve the desired pulse repetition frequency. A high voltage trigger pulse applied to conductor 60 triggers the discharge device by forming an ionized path directly from the inner end of the bare portion 60a of conductor 60 to the cathode 52, whereupon the voltage across capacitor 40 causes a spark discharge between the anode and cathode and rapid discharge of the capacitor. This rapid electrical discharge creates a shock-wave, not unlike that caused by an explosion, within bore 42 which emerges from opening 46a with explosive force. Since the shock-wave emerges from a very small bore tube, it is quasi-unidirectional, meaning that the main energy is propagated in one direction with very low beam spread so as to form, in the far field, a short duration high energy acoustic wave or pulse which, upon striking the surface of a test object induces vibrations and relaxation frequencies very similar to those produced when the surface is "tapped" with a pencil, for example. In an implementation which has been successfully operated, capacitor 40 consisted of three capacitors each having a capacitance of 0.02 microfarad, and put out about one joule of energy; that is, equal to one watt of energy discharged in a period of a second. When this one joule of energy is instead discharged in a millionth of a second, the spark discharge within bore 42 has an energy of one million watts. Other configurations can be employed for causing greater or less energy at longer or shorter pulse durations.

Figure 7:
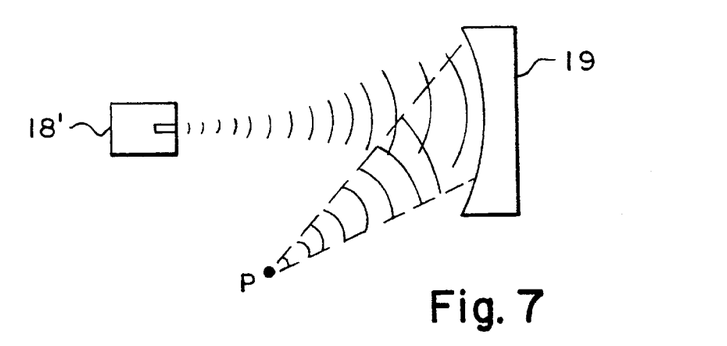
FIG. 7 is a diagrammatic elevation view of another arrangement for focusing an acoustic pulse on a test object.

Referring to FIG. 7, it is within the contemplation of the invention to direct the output of a single discharge device 18' toward an acoustic focusing lens 19 designed to focus the energy collected by the lens (less losses) to a spot at a given distance P dependent on the physical parameters of the entire system. However, the arrangements of multiple discharge devices shown in FIGS. 1, 3 and 4 are preferred because of their focusing flexibility and their ability to produce higher energy far-field acoustic pulses.

Figure 5:
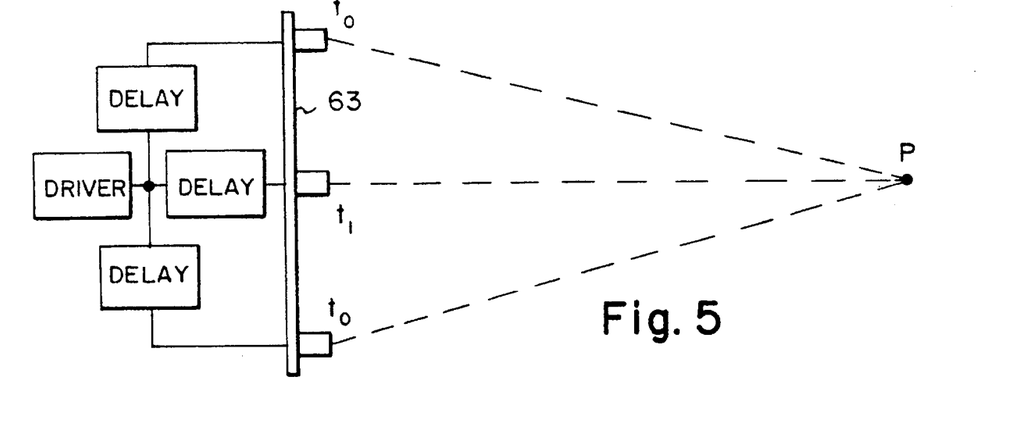
FIG. 5 is a diagrammatic elevation side view of an alternative array of acoustic pulse generating devices.

Another possible arrangement is shown in FIG. 5, wherein multiple discharge devices, three of which are visible, are arranged on a common support 63 and fired in a sequence such as to form a phased array with a common wavefront focused at a remote point P determined by the phase delays of the system. For example, the two outer spark gaps may be fired at time $t_0$, and the central discharge device, because it is nearer the desired focal point P, is fired later, at time $t_1$, so that all three wavefronts arrive at point P at the same time. Moreover, the delay system may be arranged to not only focus variably along the Z-axis, but also variably through both the "X" and "Y" axes, whereby the point of focus can be scanned to excite local areas of a test object located at a known but variable distance. This type of acoustic phased focus and scanning is known in the prior art.

Figure 6:
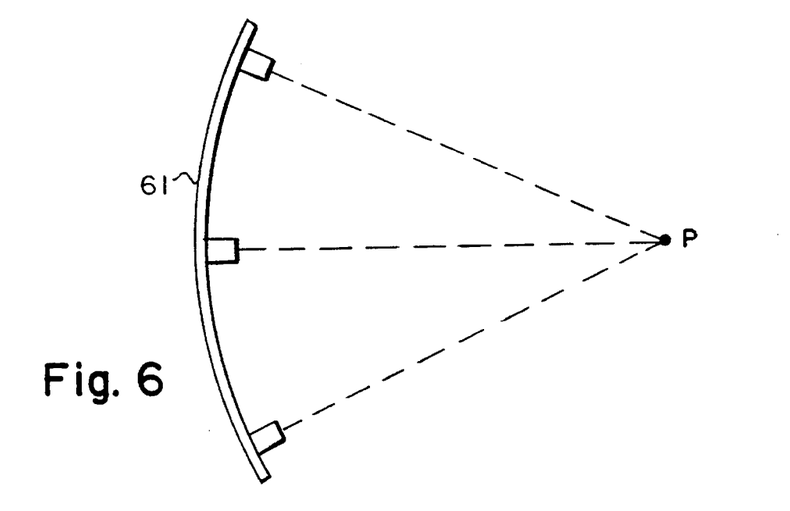
FIG. 6 is a diagrammatic elevation side view of another alternative array of acoustic pulse generating devices.

FIG. 6 shows yet another arrangement for focusing to a single spot the shock-waves generated by a plurality of simultaneously fired discharge devices. In this structure, a plurality of spark gaps, three of which are visible, are supported on a spherical dish structure 61 such that they point to a focus at the radius of curvature of the dish.

However the discharge device or devices are configured, it is essential to the operation of the invention that the duration, bandwidth and frequency of the acoustic wave impinging on the test object be much less than the relaxation frequencies or relaxation characteristics of the material or structure being tested, including the fault areas.

Before describing the laser Doppler portion of the system, the phenomena produced when the surface of a test object is "tapped" with an acoustic pulse or wavefront will be briefly summarized. If a damaged area of a composite material, for example, is tapped, there is a change in the tap noise from what is heard when a fault-free area is tapped, which indicates that the surface of the material moves differently where there is damage than where the material is sound, i.e., free of damage or fault. Furthermore, in the vicinity of a fault, whether it be on the surface or internal, following excitation by the "tap", the material exhibits relaxation frequencies which are different from those exhibited by a fault-free area of the composite material. A crude analogy might be the way an imperfect bell rings down or rings up in frequency after being struck. Differences in out-of-plane displacement between damaged and sound areas, and differences in relaxation frequencies exhibited by damaged and sound areas, both of which are excited by "tapping" the surface with remotely generated acoustic pulses, are both relevant and are utilized to ascertain the location and extent of faults.

Figure 8:
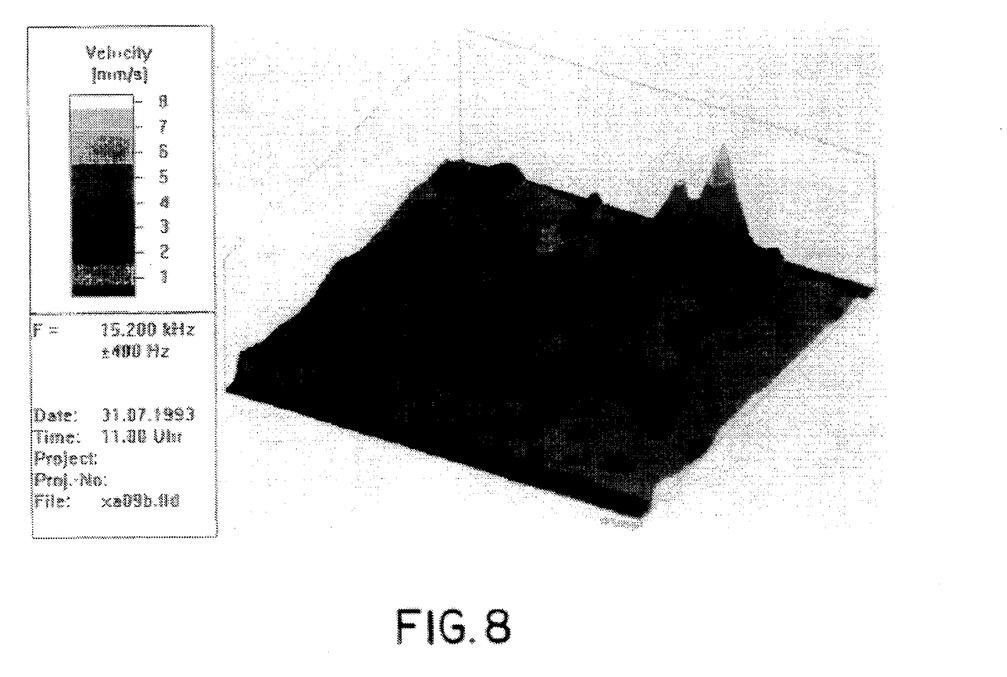
FIG. 8 is a color printout of a laser Doppler system illustrating how a fault in a tested material is manifested.

Reverting to FIG. 1, under control of a scanning controller 70, itself controlled by programmed controller 28 and synchronized with the X-Y scan control 32, a laser Doppler camera system 72 directs a laser beam, i.e., a beam of coherent light, onto a beam splitter 74 and scans a beam 75 over a selected area of interest of the test object 10 in unison with the scanning of acoustic pulses. Accordingly, as each point 10a, 10b, etc. on the surface of the object is excited, that is, "tapped" by an acoustic pulse, it is simultaneously being illuminated by a narrow laser beam. Light reflected back from the illuminated point is directed by beam splitter 74 onto laser Doppler camera 72 which detects shifts in wavelength of the reflected light caused by out-of-surface displacement of the small excited area from which the light was reflected, the shifts in wavelength being indicative of whether or not a fault is present in that area of the test object. On the basis of such shifts in wavelength, laser Doppler camera 72 provides a color printout, of which FIG. 8 is representative, which indicates by different colors or monochrome tones the velocity of movement of the excited area on the surface of the test object. In this type of display, surface displacements at very low velocity are represented, for example, by blue areas, and greater movement is represented by areas of red and purple; a purple area depicts a velocity of surface movement of 5 millimeters per second. Progressively higher velocities are represented by green and yellow, the latter depicting a velocity of movement up to 8 millimeters per second. While meaningless in themselves, the colors are representative of the surface movement and the surface changes that are actually occurring as a result of being vibrationally excited by an acoustic pulse.

FIG. 8 is a color printout produced by the system of FIG. 1 which maps the movement of an area of the surface of a composite material consisting of carbon composite impregnated with resin. The peaks tipped by green and gold areas indicate the presence of a fault which, upon physical examination, turned out to be damage previously caused by an impact producing both surface cracking and subsurface delamination.

To insure that a given displacement of a point on the surface of the test object is similarly displayed by the laser Doppler camera, regardless of where on the surface the point is located, or whether the surface is planar, or at some angle or curved, a profiler 76 is interfaced with the laser Doppler camera 72. The principle of operation of profilers is well known, and they are used in many applications, including, for example, medical. The profiler nay comprise a scanning laser system or a scanning acoustic system incorporated either in the head unit or casing of the Doppler camera or immediately adjacent to it. The purpose of the profiler is to provide information to the Doppler signal analyzing computer of the angle of the exact spot on the object surface which is being interrogated by the Doppler system at any precise moment. This information enables the analyzer to compute the correct surface displacement amplitude, including the amplitude of relaxation frequencies for that spot. In other words, correct out-of-plane amplitude can only be calculated if the angle of the surface with respect to the camera axis is known. It is also necessary to mount the Doppler camera system on a relatively stable platform in order to maintain beam pointing stability. For example, although currently available laser Doppler equipment will operate satisfactorily on a surface not isolated from ambient vibrations, in many of the situations in which the present apparatus is intended to be used, say, carried in the slightly swinging basket of a "cherry-picker" for gaining access to the fuselage of a large aircraft, unless stabilized the narrow laser beam projected from the Doppler camera would also swing wildly and the information contained in the signal reflected back into the camera would be useless.

This problem may be addressed by utilizing a form of available inertial navigational device which comprises either a gyroscope signaller or an array of accelerometers incorporated in the head of laser Doppler camera 72 which will sense any changes of position of the camera and present to programmed controller 28 information regarding any X, Y and Z motion as it occurs. The programmed controller is, in turn, programmed to analyze this data, instruct the scanning controller 70 to alter the direction of the scanning laser beam, via electrical signals to the steering mirrors, as necessary to insure that the pointing stability of the laser beam of the Doppler camera is maintained at the required information point on the object.

Under control of included software, controller 28 supplies relevant data from Doppler camera 72 to an analyzer 78 in which acquired data is compared with information stored in a data storage device 80 regarding surface displacement and relaxation frequencies previously measured on a similarly excited fault-free structure constructed of the same material. Such comparison locates fault points and identifies relaxation frequencies with a view to analyzing the extent and type of the fault. The relaxation frequencies may be recorded and analyzed during a scan of the selected area, or may be recorded for subsequent analysis, after the location of a fault has been ascertained, by analysis of only data derived from the out-of-plane displacement of the excited areas.

Summarizing, programmed controller 28 interfaced with the laser Doppler camera 72 retains in memory data relating to both the amplitude of surface displacement and details of the relaxation frequencies exhibited by the interrogated area of the object, including spatial information which defines its location, so that an area exhibiting any fault conditions can later be re-interrogated. This can be achieved either by relocation and individual re-examination of the selected area, or by processing the information with data stored in the memory of the computer during the initial scan.

The computer 28 displays the acquired data on a visual display unit (VDU) 82, superimposed on a picture of the object collected by a CCD camera 84, in the form of a colored contour map of the fault area or, alternatively, by another form of marking wherein the essential data analysis of the fault area is displayed on either the same or a linked VDU or printout system. The acquired data may be displayed in quasi-real-time, or held in store for display immediately following the interrogating scan.

With suitable modification of its software and incorporation of a laser profiler, the laser Doppler system 72 and associated signal processing hardware and software may be implemented with the commercially available PSV-100 scanning laser marketed by Polytec Optromics Inc. of Auburn, Mass. This non-contact, full-field system for vibration measurements combines a laser Doppler vibrometer with a fast scanning system, signal processing circuitry, a high performance computer, video graphics and software specifically developed for rapid, automated vibration measurement and analysis. The software controls the entire measuring system, including high speed signal processor, A/D converter, laser focus and position, vibrometer electronics and video system, and is modified in the present system to also synchronize scanning of the acoustic pulses with that of the laser beam and to provide periodic trigger pulses for triggering the discharge devices at times such that acoustic pulses are produced at an optimum time with respect to the time the Doppler vibrometer beam is interrogating the same local area on the surface of the test object.

While in the system shown in FIG. 1 the acoustic pulse and laser beam are stepped or continuously scanned covering scanned areas 10a, 10b, etc. at a rate of possibly up to 100 points per second with existing technology, it is within the contemplation of the invention to scan the surface at higher rates. The computer of the Polytec Optromics laser vibrometer system has only enough power to scan and analyze about 100 samples per second which, coupled with the finite duration of the acoustic pulses and the interval between them, dictates the scanning operation. When computers having increased power are developed, which can be expected in view of past history of computer development, it should be possible to increase the sampling rate of the laser Doppler system so as to examine more closely spaced local areas of the test object. There will be a top limit on the sampling rate, however, imposed by the duration (i.e., "ring time") of the relaxation frequencies following each interrogating acoustic pulse during which such frequencies must be sensed and analyzed.

The above-described concepts and principles are equally applicable in the inspection of composite materials, monocoque or semi-monocoque structures or objects of other forms; the display of faults may differ from one type of structure to another, but once it has been determined how a particular type of fault is manifested in the display for different types of structures, the acquired displacement and relaxation frequency data that produced the display can be used as a frame of reference for identifying a fault and its extent in a like composite material and/or structure. For example, just as in the method described in the aforementioned co-pending application Ser. No. 08/011,991, in which excitations of the outer skin of a semi-monocoque structure at a particular frequency and amplitude produces an anti-nodal pattern uniquely characteristic of one of several potential types of faults, both surface and subsurface, acoustic excitation of the outer skin of the same structure will generate a combination of surface displacement and relaxation frequencies which when analyzed and displayed will present a pattern also unique to that type of fault. Whereas in the method described in this co-pending application, information relating to the integrity of the structure is obtained by recording two time-displaced holograms of the anti-nodal pattern to produce interference patterns which contour the anti-nodal patterns, in the present method patterns similar in appearance to the fringe maps of contour patterns obtained by interferometry are directly displayed and better reveal the existence of faults. Structural faults in semi-monocoque structures, such as the fuselage of an aircraft, most often occur along the lines of the frames and stringers forming the underlying structure; in the interferogram, the frames and stringer are identified by relatively fringe-free areas or lines extending horizontally or vertically across the image, and an underlying fault such as a broken stringer forms spurious patterns along the stringer. In the laser Doppler display of the present system, the areas along the frames and stringers, because they do not experience significant surface displacement when the contiguous panel is excited, may appear in, say, blue (signifying a low displacement velocity), whereas the site of a break in a stringer would have a higher displacement velocity and appear as, say, a yellow or gold spot occurring along a stringer or frame line. Thus, an operator watching the display can positively and reliably decide that there is a fault simply by looking for changes in color from the blue, normally indicative of fault-free areas, to a color which represents a higher velocity surface displacement, such as yellow or gold. That is to say, the operator is clearly presented with a fault as opposed to having to decide whether or not a fault exists.

Because the relaxation frequencies in the region of a crack in the metal skin surrounding a rivet, or in a region where there is sub-surface corrosion must be different following excitation from what they would be if there were no crack or corrosion, observance of color differences among different areas of the display gives a positive indication of the existence of a fault and further analysis, such as comparison of the acquired data with previously measured and stored data known to represent a fault of the type suspected, enables the operator to identify the fault and its extent. Thus, it is seen that the system can be used for the non-destructive inspection of a variety of different types of materials and structures, it relieves the operator from the responsibility of deciding whether or not a fault is present, and is sufficiently compact and portable to be used in a variety of situations including in-plant and field use.

While the discharge device shown in FIG. 2 and described above was designed primarily as an acoustic exciter in the present system to produce about one joule of energy, with suitable modification of its parameters it is capable of producing very short pulses of up to say 50 joules each, an enormous amount of energy which can be focused. Similarly, in design principle it could be adapted to produce longer pulse durations of very large joule ratings, in excess of 1000 joules. The emergent acoustic wave can be likened to a very high explosive which might be used to break rocks, for example. Alternatively, the device may be useful in an underwater transmitter in which, because sound waves are transmitted much more efficiently in water then in air, the output energy could be lower and the power pack designed to increase the duration of the discharge, even to milliseconds, so as to be more akin to a low explosive.

With similar design modifications the discharge device may have military use in sonic beam weapons, primarily because of its unidirectional characteristics enabling focusing and the vast quantities of sonic energy which can be focused in a single discharge, or a series of discharges at a desired frequency not limited to the 100 Hz mentioned earlier. Also, a redesigned version may have application in sub-terrestrial exploration as a replacement for existing acoustic or explosive technology.

While specific preferred embodiments have been described, it should be understood that they are exemplary in nature and not to be construed as limiting the scope of the invention as set forth in the appended claims.

I claim:

1. A discharge device for producing a substantially unidirectional high-energy acoustic wave, comprising:

an insulator formed of hard heat-resistant material having a small-diameter axial bore having two ends formed therein, the first end of which is open, a first annular-shaped electrode surrounding and positioned at the open first end of said bore, a second electrode disposed in a position to close the second end of said bore, conductor means for coupling said first and second electrodes across terminals of a source of voltage adapted to be rapidly charged and discharged, and means for periodically forming an ionized path in said bore between said first and second electrodes, the ionized path resulting in the rapid electrical discharge of the source of voltage and the production of the substantially unidirectional high-energy acoustic wave from said open first end of said bore.

2. A discharge device for producing a substantially unidirectional acoustic wave according to claim 1, wherein said means for periodically forming an ionized path includes a conductor which extends radially inward through said insulator and terminates substantially at said bore for coupling periodic trigger pulses to said bore.

3. A discharge device for producing a substantially unidirectional acoustic wave according to claim 2, wherein said apparatus further comprises an electrically insulating enclosure within which said insulator and said electrodes are enclosed, said enclosure having an axial opening aligned with the open first end of said bore through which said substantially unidirectional high-energy acoustic wave emerges.

4. A discharge device for producing a substantially unidirectional acoustic wave according to claim 2, wherein said insulator is formed of a material selected from the group consisting of ceramic, quartz, sapphire and hard, heat-resistant plastic.

5. A discharge device for producing a substantially unidirectional acoustic wave according to claim 2, wherein said bore has a diameter in the range from 1.0 to 2.0 millimeters and the duration of said discharge is less than 10 microseconds.

6. Apparatus for producing a focused high-energy acoustic wave comprising:

a plurality of discharge devices as defined in claim 1, each of the discharge devices operating to produce the high-energy substantially unidirectional acoustic wave, and means for focusing the plurality of acoustic waves produced at a point displaced from said focusing means, whereby a focused high-energy acoustic wave is provided at said point.

7. Apparatus for producing a focused high-energy acoustic wave according to claim 6, wherein said apparatus includes a plurality of the discharge devices arrayed on a spherical dish structure to focus the high-energy substantially unidirectional acoustic waves at the center of the radius of curvature of said dish structure.

8. Apparatus for producing a focused high-energy acoustic wave according to claim 6, wherein said apparatus includes a plurality of the discharge devices supported in an array and all of the discharge devices aimed to produce high-energy unidirectional acoustic waves travelling in the same general direction, and means for firing said arrayed discharge devices in a sequence to form a common wavefront for the high-energy acoustic waves that is focused at a selectable variable distance from the array determined by the firing sequence of said discharge devices.

9. Apparatus as defined in claim 8 for producing a focused high-energy acoustic wave over a predetermined scanning pattern, wherein said means for firing includes a delay system for timing the firing of the discharge devices to focus variably the substantially unidirectional high-energy acoustic waves along a Z-axis of the array and variably through orthogonal X- and Y-axes of the array, whereby the point of focus is scanned over the said predetermined scanning pattern.

10. Apparatus for producing a focused high-energy acoustic wave comprising a single discharge device as defined in claim 1, means for focusing the substantially unidirectional high-energy acoustic wave produced by the discharge device, said focusing means including an acoustic focusing lens for focusing the acoustic wave produced by said discharge device at a spot displaced from said lens by a predetermined distance.

* * * * *